United States Patent [19]

Bensalem

[11] 4,057,649

[45] Nov. 8, 1977

[54] METHOD OF TREATING FOOD PRODUCTS WITH SELENIUM SALTS

[76] Inventor: Djemal Eddine Bensalem, 6, rue Charles Valin, Alger, Algeria

[21] Appl. No.: 572,198

[22] Filed: Apr. 28, 1975

[30] Foreign Application Priority Data

Apr. 26, 1974 France .............................. 74.14574

[51] Int. Cl.$^2$ .............................................. C12G 1/00
[52] U.S. Cl. ....................................... 426/15; 426/17; 426/19; 426/60; 426/322; 426/330.4; 426/335; 426/532
[58] Field of Search ................. 426/321, 335, 322, 60, 426/19, 15, 11, 17, 74, 648, 330.3, 330.4, 335, 532; 424/131, 162–165

[56] References Cited

U.S. PATENT DOCUMENTS 3,404,987 10/1968 Kooistra .......................... 426/322 X Primary Examiner—R. B. Penland
Attorney, Agent, or Firm—Bacon & Thomas

[57] ABSTRACT

The invention relates particularly but not exclusively to the basic food products consumed by human beings.

The method of improving and retaining the nutritional qualities of basic foods and drinks consists in incorporating in these products, after the final stage of normal usefulness of the yeasts contained therein, an antimycotic product such as selenium sulphide or any selenium salt or heavy-metal salt.

The method is applied by adding very small quantities of selenium sulphide to bread, wines, beer and other foods and beverages requiring the addition of yeasts for preparing them for consumption.

The method of the invention may also be applied in the treatment of products other than food products, for example tooth-pastes, bottles, under-garments and medical equipment made of plastics materials.

8 Claims, No Drawings

METHOD OF TREATING FOOD PRODUCTS WITH SELENIUM SALTS

FIELD OF THE INVENTION

The present invention relates to the treatment of products used in food, beverages and clothing and for hygienic purposes and the general care of human beings. One important aspect of the invention is concerned with basic food products, that is to say solid or liquid foods that have been consumed regularly by human beings for many generations because of their undisputed nutritional value, e.g. bread, wines, beer, spirits, vinegar etc.

BACKGROUND OF THE INVENTION

The medical profession, relying on a large number of dietetic studies, often prescribes in numerous cases that patients should not consume these foods during periods of varying length.

It is surprising that such a measure should be taken against foods that have been used so universally and over such lengthy periods. It is therefore not difficult to imagine that such prohibition has resulted from incomplete knowledge of the biochemical composition of these foods and, in particular, incomplete knowledge of the real reason why they can become harmful to the human organism.

One of the objects of the present invention is that of reinstating these foods by suggesting a probable cause of these physiological troubles and by indicating a remedy whereby said cause can be removed partially or completely.

The present applicant has devoted considerable time to this matter and to deep studies on various physiological troubles such as diabetes and dental decay. Whereas these illnesses appear to be unconnected, these studies have shown that in all probability there exists a common cause leading to the occurrence and development of these infections and that this cause lies in the fermentation yeasts and the mycotic substances, such as candidotic substances, which circulate in the digestive tracts.

It is well-known that fermentation is an archaic anaerobic practice which opposes respiration which is a fundamental essential of the higher organisms. Consequently if these yeasts, as used in baking, brewing, wine-making etc., are allowed to penetrate the human or animal organism, they will act as anti-oxidants.

After having fulfilled their industrial purpose in the preparation of foods, these yeasts continue to exist and to promote fermentation, since bread becomes stale, wine changes into vinegar, and beer becomes cloudy and spoils. Since these foods and beverages are consumed prior to this stage, the yeasts will continue to multiply in the organism thereby causing fermentation which will promote the proliferation of mycotic substances such as candidotic substances and others in the human body, such fermentation opposing the enzymatic respiratory systems of the human being. In certain individuals, the opposition offered may reach the stage where the phenomenon of fermentation is followed by the various physiological troubles enumerated above.

It has thus been shown that it is desirable to eliminate or destroy these yeasts by means of a suitable antimycotic product before they pass into the human body.

DESCRIPTION OF THE INVENTION

The object of the present invention is to provide a method of treating products used in food, beverages and clothing and for hygienic purposes and the general care of human beings, with a view to eliminating the secondary effects of industrial yeasts or saprophytes as they are considered to be, which method is characterized in that there is suitably incorporated in these products an anti-mycotic adjuvant such as selenium sulphide or any selenium salt or heavy-metal salt, the products thus treated acting through an internal or external path.

In the case of bread, this salt will be added to the already fermented dough just before baking; for wines and beer, the addition will be made just prior to bottling.

Naturally, the doses will be extremely small, for example 2 to 5 parts per million, since these foods and beverages which are consumed constantly will become slightly medicated; through permanent action, the salts will not only attack the residual yeasts in these foods and beverages, but also the mycotic substances such as candidotic substances that live in the human body. When determining these doses, it will be necessary to take into account that, since the above-mentioned foods and beverages are consumed daily and simultaneously, the various doses added to each of them will be cumulative in the organism.

It should not be deduced from the idea underlying the invention that suppression of the use of industrial yeasts is advocated; these will always have a function to perform, but the applicant considers that their action, when prolonged beyond the useful stage, will be of the same kind as the action of yeasts of a pathogenic nature and will reinforce this latter action. Also, industrial yeasts undergo mutations which generate forms having different properties which are almost pathogenic. It is therefore necessary to recognize that the action of residual yeasts in constantly consumed food and drinks contributes to what is called the pathology of civilization i.e. caries, diabetes, rickets etc.

In support of these views, some of the obvious proofs of this cause of pathology are given below:

Apart from the work carried out by the applicant on caries and diabetes attention is drawn to the internationally known diet for rickets sufferers adopted in 1926 and known as the Steenbeck and Black diet.

The action of selenium salts - see the American and French works referred to above.

The prohibition of certain food and beverages imposed by the medical and dietetic professions.

Pathogenic interference by yeasts takes place in the following way:

Their action is focussed on the general metabolism in that they compete in an inhibitive manner with the cells of the organism when the Biotin enzymatic system or vitamin $B_8$-magnesium are used. Vitamin $B_8$ intervenes in the basic reactions to promote:

the Krebs cycle,
the lipid cycle, and
the metabolism of proteins and RNA

The Krebs cycle is the veritable power-house of all breathing animal species, and particularly that of man. This cycle takes place in the mitochondria, and it is obvious that the administering of Biotin will render the mitochondria useless, so that a considerable loss of energy results.

The accounts for the fatigue that accompanies all pathological conditions and for the inability of the mitochondria to effect other no less vital biochemical cycles; for example mineralization of $Ca^{++}$ can no longer take place.

Thus, the lack of energy will inhibit mobilization of the $Ca^{++}$ ion, which is the most important constituent in the economics of the human body. This is commonly known as demineralization which is accompanied by lack of contractility, the occurrence of hyper-excitability or hypo-excitability etc.

It is on account of the complete unawareness of these phenomena that use has been made of yeasts in food and beverages for human consumption, but it is unthinkable at present that the use of these yeasts can be suppressed. The aim of the invention is therefore to improve them by maintaining their nutritional properties or gastronomic properties (in wines and cheeses for example), while at the same time eliminating those forms of yeasts likely to inhibit the enzymatic systems and to cause people to live their lives at a slower pace and/or to contract one of the illnesses of civilization as they are called.

The beneficial role of the introduction of anti-mycotic products such as selenium sulphide into food and drink is thus proved by the fact that by suppressing the use of yeasts it would be possible to lengthen the period over which these foods and drinks could be preserved.

Granted this special anti-pathogenic function of selenium sulphide, it is possible to think of ways in which its use can be extended, for example in tooth-pastes for the purpose of externally combating dental decay.

People suffering from skin diseases are automatically advised against wearing under-garments made of synthetic fibres. This prohibition could be lifted if, prior to weaving, the synthetic fibres are plunged in a selenium sulphide bath.

Finally, bottles and other containers made of synthetic resins as well as medical equipment made of plastics material, particularly catheters and syringes, could undergo "sterilization", as it were, in selenium sulphide, since these materials have a certain pathogenic capacity in the sense that they promote rapid breeding within the yeasts.

In these last-mentioned applications (clothes and equipment made of synthetic resins) the selenium salts may be introduced in doses in the order of 1 to 10%, for example.

The embodiments of the invention in which an exclusive property or privilege is claimed are defined as follows:

1. In a method of preparing a nutrititional material from foodstuffs, including the step of fermentation of said nutritional material with a yeast, the improvement consisting essentially of incorporating into said nutritional material after said fermentation, an effective amount of an anti-mycotic adjuvant to minimumize the effect of residual yeast wherein said adjuvant is a selenium salt.

2. A method according to claim 1 wherein said nutritional material is bread and said anti-mycotic adjuvant is incorporated after fermentation and rising of a dough and before baking of said dough.

3. A method according to claim 1 wherein said nutritional material is a beverage selected from beer and wine, and said anti-mycotic adjuvant is incorporated into said beverage immediately before bottling.

4. A method according to claim 1 wherein said nutritional material is vinegar and said anti-mycotic adjuvant is incorporated into said vinegar immediately before bottling.

5. A method according to claim 1 wherein said effective amount is from about 2 to about 5 parts by million.

6. A method according to claim 5 wherein said nutritional material is selected from the group consisting of beer, wine and vinegar.

7. The method of claim 1 wherein the adjuvant is selenium sulphide.

8. The method of claim 5 wherein the adjuvant is selenium sulphide.

* * * * *